United States Patent
Kotler et al.

[19]

[11] Patent Number: 5,865,763
[45] Date of Patent: *Feb. 2, 1999

[54] METHOD FOR ESTIMATING CREATININE CLEARANCE IN OBESE AND MALNOURISHED SUBJECTS USING MEASUREMENTS OF BODY CELL MASS

[75] Inventors: Donald P. Kotler, New Rochelle; Emilia M. Sordillo, New York, both of N.Y.

[73] Assignee: St. Luke's-Roosevelt Hospital, New York, N.Y.

[*] Notice: The term of this patent shall not extend beyond the expiration date of Pat. No. 5,722,396.

[21] Appl. No.: 854,380

[22] Filed: May 12, 1997

Related U.S. Application Data

[63] Continuation-in-part of Ser. No. 694,615, Aug. 13, 1996, Pat. No. 5,722,396.

[51] Int. Cl.$^6$ ..................................................... A61B 5/05
[52] U.S. Cl. ............................................ 600/547; 600/300
[58] Field of Search ..................................... 600/300, 547

[56] References Cited

U.S. PATENT DOCUMENTS 5,722,396  3/1998  Kotler et al. ............................ 600/300

OTHER PUBLICATIONS

F. D. Moore et al., "The Body Cell Mass And Its Supporting Environment," W.B. Saunders Co. (1963).
R. B. Darlington, "Regression and Linear Models," McGraw-Hill Publishing Co. pp. 369–370 (1990).
S. B. Heymsfield et al., "Measurement of Muscle Mass In Humans: Validity Of The 24–Hour Urinary Creatinine Method," 37 *Am. J. Clin. Nutr.*, pp. 478–494 (1983).
R. Hatala et al. "Once–Daily Aminoglycoside Dosing In Immunocompetent Adults: A Meta–Analysis," 124 *Ann. Intern. Med.*, pp. 717–725 (1996).

D. P. Kotler et al., "Prediction of Body Cell Mass, Fat–Free Mass, and Total Body Water With Bioelectrical Impedance Analysis: Effects of Race, Sex, and Disease," 64 *Am. J. Clin. Nutr.*, pp. 489S–497S (1996).
S. B. Miller, "Renal Diseases," in *The Washington Manual: Manual of Medical Therapeutics*, Boston, Little, Brown, pp. 262–278 (27$^{th}$ ed. 1992).
J. S. Bertino, Jr., "Measured Versus Estimated Creatinine Clearance In Patients With Low Serum Creatinine Values," 27 *Ann. Pharmacotherapy*, pp. 1439–1441 (1993).
R. W. Jelliffe, "Creatinine Clearance: Bedside Estimate," 79 *Ann. Int. Med.*, pp. 604–605 (1973).
D. W. Cockcroft et al., "Prediction of Creatinine Clearance from Serum Creatinine," 16 *Nephron*, pp. 31–41 (1976).
D. N. Gilbert, "Aminoglycosides," in *Mandell, Douglas and Bennett's Principles and Practices of Infectious Diseases*, Churchill Livingstone, pp. 279–306 (4$^{th}$ ed. 1995).
K. Siersback–Nielsen et al., "Rapid Evaluation of Creatinine Clearance," 1 *Lancet*, pp. 1133–1134 (1971).
K. R. Segal et al., "Estimation of Human Body Composition By Electrical Impedance Methods: A Comparative Study," 58 *J. Appl. Physiol.* pp. 1565–1571 (1985).
W. R. Schiller, "Creatinine and Nitrogen Excretion in Seriously Ill and Injured Patients," 149 *Surg. Gyn. & Ob.*, pp. 561–566 (1979).

(List continued on next page.)

*Primary Examiner*—Francis J. Jaworski
*Attorney, Agent, or Firm*—Baker & Botts, L.L.P.

[57] ABSTRACT

Creatinine clearance is estimated in a patient by determining his or her body cell mass. In turn, the body cell mass of the patient is measured using bioimpedance analysis techniques. The patient's serum creatinine concentration is also measured. The body cell mass and the serum creatinine concentration provide an indication of actual creatinine clearance in the subject through use of a predictive formula. From this prediction, accurate dosages of potentially nephrotoxic medications can be appropriately prescribed.

9 Claims, 10 Drawing Sheets

OTHER PUBLICATIONS

T. D. Bjornsson, "Use of Serum Creatinine Concentrations to Determine Renal Function," 4 *Clin. Pharmacokinetics,* pp. 200–202 (1979).

G. F. Gates, "Creatinine Clearance Estimation From Serum Creatinine Values: An Analysis of Three Mathematical Models of Glomerular Function" 5 *Am. J. Kidney Dis.,* pp. 199–205 (1985).

T. Hallynck et al., "Prediction of Creatinine Clearance from Serum Creatinine Concentration Based on Lean Body Mass," 30 *Clin. Pharmacology and Theradeutics,,* pp. 414–421 (1981).

M. B. O'Connell et al., "Predictive Performance of Equations to Estimate Creatinine Clearance in Hospitalized Elderly Patients," 26 *Ann. Pharmacotherapy,,* pp. 627–635 (1992).

R. N. Sladen, "Accurate Estimation of Glomerular Filtration in the Intensive Care Unit: Another Holy Grail?" 21 *Crit. Care Medicine,* pp. 1424–1427 (1993).

S. Robert et al., "Predictability of Creatinine Clearance Estimates in Critically Ill Patients," 21 *Crit. Care Medicine,* pp. 1487–1495 (1993).

R. Skinner et al., "Inaccuracy of Glomerular Filtration Rate Estimation From Height/Plasma Creatinine Ratio," 70 *Arch. Dis. Childhood,* pp. 387–390 (1994).

T. M. S. Wolever, "Effect of Meal Frequency on Serum Amino Acids and Creatinine Clearance in Young Men," 307 *Am. J. Med. Sciences,* pp. 97–101 (1994).

E. G. Boyce et al., "Creatinine Clearance Estimation in Protein–Malnourished Patients" 8 *Clin. Pharmacy,* pp. 721–726 (1989).

C. Martin et al., "Assessment of Creatinine Clearance in Intensive Care Patients" 18 *Crit. Care. Med.,* pp. 1224–1226 (1990).

W. T. Sawyer et al., "Variables Affecting Creatinine Clearance Prediction," 40 *Am. J. Hosp. Pharm.,* pp. 2175–2180 (1983).

W. T. Sawyer et al., "A Multicenter Evaluation of Variables Affecting the Predictability of Creatinine Clearance," 78 *Am. J. Clin. Path.,* pp. 832–838 (1982).

A. H. Lau et al., "Estimation of Creatinine Clearance in Malnourished Patients," 7 *Clin. Pharmacy,* pp. 62–65 (1988).

M. M. Chrymko et al., "Creatinine Clearance Predictions in Acutely Ill Patients," 38 *Am. J. Hosp. Pharm.,* pp. 837–840 (1981).

M. Smythe et al., "Estimating Creatinine Clearance in Elderly Patients with Low Serum Creatinine Concentrations," 51 *Am. J. Hosp. Pharm.,* pp. 198–204 (1994).

L. L. Caregaro et al., "Limitations of Serum Creatinine Level and Creatinine Clearance as Filtration Markers in Cirrhosis" 154 *Arch. Int. Med.,* pp. 201–205 (1994).

R. E. Dionne et al., "Estimating Creatinine in Morbidly Obese Patients," 38 *Am. J. Hosp. Pharm.,* pp. 841–844 (1981).

M. A. Smythe et al., "Relationship Between Values of Bioelectrical Impedance and Creatinine Clearance," 10 *Pharmacotherapy,* pp. 42–46 (1990).

R. F. Kushner et al., "Estimation of Total Body Water by Bioelectrical Impedance Analysis 1," 44 *Am. J. Clin. Nutr.,* pp. 417–421 (1986).

O. M. Edwards et al., "Urinary Creatinine Excretion as an Index of the Completeness of 24–Hour Urine Collections," 2 *Lancet,* pp. 1165–1166 (1969).

A. S. Levy et al., "Laboratory Assessment of Renal Disease: Clearance, Urinalysis, and Renal Biopsy," in *The Kidney,* pp. 919–968, W.B. Saunders Co. ($4^{th}$ ed. 1991).

K. R. Segal et al., "Lean Body Mass Estimation by Bioelectrical Impedance Analysis: A Four–Site Cross–Validation Study," 47 *Am. J. Clin. Nutr.,* pp. 7–14 (1988).

H. C. Lukaski et al., "Assessment of Fat–Free Mass Using Bioelectrical Impedance Measurements of the Human Body," 41 *Am. J. Clin. Nutr.,* pp. 810–817 (1985).

J. M. Bland et al., "Statistical Methods for Assessing Agreement Between Two Methods of Clinical Measurement," *Lancet,* pp. 307–310 (1986).

J. S. Bertino et al., "Incidence of and Significant Risk Factors for Aminoglycoside–Associated Nephrotoxity in Patients Dosed by Using Individualized Pharmacokinetic Monitoring," 167 *J. Inf. Dis.,* pp. 173–179 (1993).

B. L. Kasiske et al., "Laboratory Assessment of Renal Disease: Clearance, Urinalysis, and Renal Biopsy," in *The Kidney,* pp. 1137–1174, W.B. Saunders Co. ($5^{th}$ ed. 1996).

FIG. 3A COCKCROFT-GAULT (WEIGHT)

METHOD FOR ESTIMATING CREATININE CLEARANCE IN OBESE AND MALNOURISHED SUBJECTS USING MEASUREMENTS OF BODY CELL MASS

SPECIFICATION

This application is a continuation-in-part of U.S. Ser. No. 08/694,615, filed Aug. 13, 1996 and now U.S. Pat. No. 5,723,396, entitled METHOD FOR ESTIMATING CREATININE CLEARANCE USING MEASUREMENTS OF BODY CELL MASS, now pending.

FIELD OF THE INVENTION

The present invention relates to a method for estimating creatinine clearance in obese or malnourished human subjects which is particularly suitable for determining appropriate dosages of medication, in order to avoid or prevent adverse drug reactions and toxicity.

BACKGROUND OF THE INVENTION

Dosing regimens for several drugs used in treating renal diseases, most notably the aminoglycosides, are based upon a measurement of renal function known as the glomerular filtration rate (GFR). It is often necessary to estimate GFR, since actual measurement is both expensive and time-consuming. However, standard methods for estimating renal function are prone to errors which can result in inaccurate drug dosages being prescribed to an individual. These inaccuracies have created substantial risk of nephrotoxicity in underweight patients and insufficient dosages being prescribed to overweight or obese subjects.

The reported incidence of aminoglycoside nephrotoxicity ranges from 0–50%, with rates in most studies in the 5–25% range. Prospective studies that defined nephrotoxicity as a substantial decrease in the GFR reported an incidence of nephrotoxicity that ranged from 5–10% in severely ill patients. Aminoglycoside toxicity can be minimized if such drugs are dosed appropriately.

In clinical practice, renal function can be estimated through measurement of inulin clearance ($CL_{IN}$) or creatinine clearance ($CL_{CR}$). Measurement of $CL_{IN}$ is preferred by many clinicians because inulin is an inert sugar that is cleared solely by glomerular filtration. Because inulin is neither secreted nor absorbed by the renal tubules, it is believed to be a relatively accurate indicator of GFR.

However, measurements of $CL_{IN}$ can vary by as much as 20% in an individual at a given time. In addition, determination of $CL_{IN}$ is not practical in an everyday clinical setting. The procedure requires intravenous infusion of inulin followed by three timed urine collections. Thus, measurement of $CL_{IN}$ is laborious, time-consuming and expensive.

Measurement of $CL_{CR}$ is a practical substitute for $CL_{IN}$ in estimating renal function. Creatinine, which is a product of muscle metabolism, is eliminated by the kidneys mainly by glomerular filtration, but also to a minor extent by tubular secretion. For this reason, $CL_{CR}$ measurements usually overestimate the GFR in comparison to $CL_{IN}$. However, $CL_{CR}$ measurement is simpler and less expensive to perform.

There are several methods for estimating $CL_{CR}$. The standard method involves collecting the urine output ($V_U$) from a subject for a 24-hour period and measuring urine ($U_{CR}$) and serum ($S_{CR}$) creatinine concentrations. Creatinine clearance is then calculated as:

$$CL_{CR}=(U_{CR})(V_U)/(S_{CR})$$

Some studies suggest that shorter collection periods (i.e. 30 minutes to two hours) are as predictive of GFR as the 24-hour collection period. However, many patients who are admitted to a hospital require urgent administration of aminoglycosides or other potentially toxic medications in a time frame that does not allow for such measurements of $CL_{CR}$.

Because of this, a number of authors have developed mathematical equations to estimate GFR. The equation that is most commonly used in clinical practice is the Cockcroft-Gault (C-G) equation. There are different forms of the C-G equation that use either ideal body weight or actual body weight. The C-G equation using ideal body weight for male subjects is expressed as:

$$\text{Estimated Male } CL_{CR}=[(140-\text{age})\times IBW/(72\times S_{CR})]$$

where IBW and age refer to a patient's ideal body weight (kg) and physical age, respectively. For female subjects, the corresponding C-G equation is:

$$\text{Estimated Female } CL_{CR}=(0.85\times\text{Estimated male }CL_{CR}).$$

In turn, ideal body weight is calculated as:

$$\text{Male } IBW\ (kg)=50+[2.3\times(\text{Height in inches}-60)]$$

$$\text{Female } IBW\ (kg)=45+[2.3\times(\text{Height in inches}-60)]$$

The above C-G equations assume that a subject is in a steady-state, that skeletal mass is a constant percentage of weight and that deviations from ideal weight do not affect renal function. However these assumptions may not be true, particularly in cases where a patient is malnourished or severely ill, thereby diminishing the accuracy of renal function determination using the C-G equations. It has been determined, in fact, that the C-G equations are prone to error, especially where a subject's body weight varies from his or her IBW.

Moreover, individual variables in the equation such as age, $S_{CR}$, IBW, height and sex do not correlate with measured $CL_{CR}$. Actual body weight as a percent of ideal, however, correlated with $CL_{CR}$, suggests that the C-G equations systematically overestimate $CL_{CR}$ in subjects below IBW and underestimate $CL_{CR}$ in subjects over IBW. A physician relying on these equations would, thus, over-prescribe medication for underweight subjects and under-prescribe medications in overweight patients.

Substitution of actual weight for IBW in the C-G equation somewhat improved the prediction of $CL_{CR}$. Still, published case series have reported an incidence of aminoglycoside nephrotoxicity ranging from 0 to 25% based upon use of the C-G equations. In light of this, several other authors have made attempts at improving predictive formulae.

Boyce et al. concluded that the C-G equation used with the lower of either ideal or actual weights was the most precise and least biased method for testing malnourished patients. E. G. Boyce et al., *Creatinine Clearance Estimation in Protein-Malnourished Patients*, 8 Clin. Pharm. 721, 726 (1989).

M. Smythe et al. concluded that in elderly patients with low $S_{CR}$, correcting serum creatinine in the C-G equations to 1.0 mg/dL led to underestimates of both $CL_{CR}$ and the dosages of aminoglycosides. M. Smythe et al., *Estimating Creatinine Clearance in Elderly Patients with Low Serum Creatinine Concentrations*, 51 Am. J. Hosp. Pharm. 198, 204 (1994).

O'Connell et al. found the Jelliffe 1973 equation using modified lean body weight was best for predicting the correct drug doses for hospitalized elderly patients. M. B. O'Connell et al., *Predictive Performance of Equations to Estimate Creatinine Clearance in Hospitalized Elderly Patients*, 26 Ann. Pharmacother. 627, 635 (1992).

Bertino concluded that in patients with an $S_{CR}$ Of less than 1.0 mg/dL, the actual $S_{CR}$ level should be used when calculating $CL_{CR}$ by the C-G equations. J. S. Bertino, Jr., *Measured Versus Estimated Creatinine Clearance in Patients with Low Serum Creatinine Values*, 27 Ann. Pharmacother. 1439, 1441 (1993).

Only two studies of renal function are known to have used bioimpedance analysis (BIA) to predict $CL_{CR}$. In the first, reported by A. S. Smythe et al., *Relationship Between Values of Bioelectrical Impedance and Creatinine Clearance*, 10 Pharmacotherapy 42, 46 (1990), BIA was performed on 28 healthy adult volunteers. They measured $CL_{CR}$ using 24-hour urine collection and calculated $CL_{CR}$ using seven predictive formulae.

Multiple linear regression analysis of the findings of Smythe et al. revealed that measured $S_{CR}$ and resistance (R), determined by BIA were significant predictors of measured $CL_{CR}$. The authors derived a predictive equation:

$$CL_{CR} = 288.3 - 0.202(R) - 66.64(S_{CR})$$

The mean absolute prediction error for $CL_{CR}$ determined by this method was significantly lower than those obtained from 4 of 7 standard $CL_{CR}$ predictive equations.

In the second study, S. Robert et al., *Predictability of Creatinine Clearance Estimates in Critically Ill Patients*, 21 Crit. Care Med. 1487, 1495 (1993), $CL_{IN}$ was used as the criterion method for GFR, from which $CL_{CR}$ was calculated using 30-minute and 24-hour urine collection techniques. The authors utilized BIA to measure lean body mass (LBM) and then used LBM in place of weight in the C-G equation to predict $CL_{CR}$ with a corrected $S_{CR}$.

In this latter study, LBM and a corrected $S_{CR}$ tended to overestimate the GFR. The research concluded that equations using the lower of IBW or actual body weight along with a corrected $S_{CR}$ were significantly better predictors of $CL_{IN}$ than either the 30-minute or 24-hour urine collection techniques. However, the results of Robert et al. indicate a greater than 20% disparity between the modified C-G equations and $CL_{IN}$ in 55% of their subjects.

With the inconclusive and varied results above, the issues of how to best express weight in the calculation and whether or not to correct $S_{CR}$ in the C-G equations remain unresolved. Furthermore, no equations have yet been determined which can apply to all groups of patients, regardless of such factors as age, race, gender, nutritional status, or those affected by disease. Improving the prediction of $CL_{CR}$ could decrease the incidence of nephrotoxicity independent of dosing frequency, which could in turn lead to cost savings in medical care.

SUMMARY OF THE INVENTION

In accordance with the present invention, a method for predicting creatinine clearance in one or more patients is disclosed whereby body cell mass (BCM) is measured to estimate creatinine clearance. Preferably, BCM is determined by performing bioimpedance analysis (BIA) on a subject and using the results to calculate BCM according to previously derived formulae. It is preferable that the serum creatinine concentration ($S_{CR}$) of the subject is also measured. In particular, creatinine clearance is estimated according to the equation: $CL_{CR} = 4.81(BCM) - 97.11(S_{CR}) + 69.7$.

BCM has a correlation with measured $CL_{CR}$ which is stronger than actual body weight. An estimate of creatinine clearance can be determined directly from the calculation of BCM.

An object of the present invention is to provide a method for estimating the creatinine clearance of a patient which is more accurate than other known methods for such estimation.

A further object of the present invention is to provide a method for estimating the creatinine clearance which is clinically practical and more accommodating than actual creatinine clearance measurement.

A still further object of the present invention is to provide a method for determining creatinine clearance which is independent of such variables as the patient's age, race, gender, actual or ideal body weight, nutritional status, or affliction with disease.

A still further object of the present invention is to provide a method for determining creatinine clearance which allows for proper dosing of potentially nephrotoxic or other medications in the treatment of renal disease.

Further objects of the invention will readily appear to those skilled in the art from a review of the invention as disclosed.

BRIEF DESCRIPTION OF THE DRAWINGS

Further objects, features and advantages of the invention will become apparent from the following detailed description taken in conjunction with the accompanying figures in which.

Throughout the figures, the same reference numerals and characters, unless otherwise stated, are used to denote like features, elements, components or portions of the illustrated embodiment. Moreover, while the subject invention will now be described in detail with reference to the figures, it is done so in connection with preferred embodiments. It is intended that changes and modifications can be made to the described embodiments without departing from the true scope and spirit of the subject invention as defined by the appended claims.

DETAILED DESCRIPTION OF THE INVENTION

A study was performed using 122 subjects (55 in New York and 67 in San Francisco), including 97 men and 25 women, in order to determine a more accurate method for estimating creatinine clearance ($CL_{CR}$) and for determining the accuracy of the Cockcroft-Gault (C-G) equations in determining $CL_{CR}$ in a patient whose weight varies from ideal.

Seventy-nine (79) of the subjects in this study had been determined to be HIV-infected, but without intrinsic renal disease, while 43 of the subjects were healthy controls. The subjects had no history of primary renal disease and were not receiving nephrotoxic drugs. Subjects' ages ranged from 19 to 65 years (mean±standard deviation=42.1±8.7). Their body weights varied from 43.2 to 111.4 kg (71.6±14.4) or 56 to 194% of ideal. Serum creatinine concentrations ($S_{CR}$) and 24 hour urinary creatinine excretions were determined by standard methods in all subjects. $S_{CR}$ ranged from 0.5 to 1.4 mg/dl (0.9±0.2) and 24-hour creatinine excretions ranged from 476 to 2,544 mg (1,433±461). $CL_{CR}$, determined from 24-hour urine collections, ranged from 36.7 to 210 ml/min (108.4±32.0).

In the study, body cell mass (BCM) analysis was chosen over analysis by body weight. By definition, the measurement of body weight alone does not allow the determination of fat, lean mass and water. Due to these deficiencies, methods have been developed to assess different body compartments. BCM is a heterogeneous compartment consisting of all non-adipose tissue cells, the aqueous components of adipocytes and the hematopoietic cells. BCM is distinct from fat, extracellular water and extracellular solids.

Classically, the size of the BCM in a patient has been difficult to estimate, since it is such a heterogeneous compartment. Techniques for obtaining certain measurements, such as total body potassium content, total body nitrogen content and intracellular water volume, are available only at a few highly specialized clinical nutrition research centers. The cost and sophistication of such techniques, however, make them unsuitable for most everyday clinical uses.

Thus, the BCM of each patient in the present study was determined using the bioimpedance analysis (BIA) techniques disclosed and claimed in U.S. patent application Ser. No. 08/353,933 of Kotler, filed on Dec. 12, 1994, now allowed, which is herein incorporated by reference. The analysis was accomplished using an RJL 101 bioimpedance analyzer manufactured by RJL Systems of Clinton Township, Mich., and purchased therefrom. Calculation of BCM was accomplished by using the Fluid and Nutrition Analysis v. 3.1 software, also marketed by RJL Systems, which incorporates the BIA formulae of Ser. No. 08/353,933.

BIA was chosen for determining renal function because the analyzer involved is portable, operator-independent, simple to learn and operate and, thus, adaptable for use in a variety of clinical settings. In addition, accuracy in the measurement of BCM by BIA is independent of variable factors such as a patient's age, race, gender, hydration status and disease. Furthermore, as shown in Ser. No. 08/353,933, BIA has proven to be an accurate evaluator of BCM.

To perform BCM analysis, the bioimpedance analyzer is affixed to a patient who is lying on his or her back on an examination table with shoes and socks removed. Two electrodes are placed on the patient's right wrist and right ankle. A current of approximately 800 microamps at 50 kHz is then delivered. Resistance (R) (the voltage drop of the applied current) and reactance (X) (opposition to electric current caused by capacitance) are measured.

In accordance with the disclosure of Ser. No. 08/353,933, a human body's ionic circuit is best represented as a parallel circuit containing capacitors. In the '933 application, the optimal exponents for height, resistance and impedance were determined using a multiple regression technique after logarithmic transformation of the data. The most accurate representations for BCM in males and females were determined to be:

$$BCM = 0.76[(59.06)Ht^{1.60}/Xc_p^{0.50}] + 18.52(Wt) - 386.66 \text{ (for males)};$$

$$BCM = 0.96[(1.30)Ht^{2.07}/Xc_p^{0.36}] + 5.79(Wt) - 230.51 \text{ (for females)};$$

where:
Ht=height of the patient (cm);
$Xc_p$=parallel transformed reactance (ohms); and
Wt=measured weight of the patient (kg).

The accuracy of the Cockcroft-Gault estimations of $CL_{CR}$ were evaluated by linear regression analysis. The relationships among measured $CL_{CR}$ and the components of the Cockcroft-Gault estimates, including weight, ideal body weight (IBW), age, sex, and height (the latter used in the prediction of IBW) were examined by multiple regression. The differences between measured and predicted $CL_{CR}$ were analyzed as a function of (measured and predicted) $CL_{CR}$ and as a function of nutritional status, defined as percent IBW, body mass index (BMI) (wt/ht$^2$), or BCM, in order to determine if there were any systematic bias in the prediction.

A predictive model for $CL_{CR}$ was derived from BIA. It was hypothesized that $CL_{CR}$ is related to BCM and to $S_{CR}$, and that BCM depletion is reflected in decreased $CL_{CR}$. The relationship between BCM and total urinary creatinine excretion, the latter a reflection of skeletal muscle mass, was examined by linear regression analysis. A prediction equation for $CL_{CR}$ was derived by multiple regression analysis with measured $CL_{CR}$ as the dependent variable and BCM and $S_{CR}$ as the independent variables. The independent, additive effects of weight, IBW, sex, height, HIV status, and site of study on this model were examined by hierarchical multiple regression analysis. The differences between measured and predicted $CL_{CR}$ were analyzed in relation to $CL_{CR}$ and nutritional status as described above to examine for possible systematic bias in the prediction.

The validity of the BIA-derived predictive model for $CL_{CR}$ was also evaluated. In addition to the correlation coefficients (r$^2$), which reflect the closeness of fit of the model to the measurements, the adjusted r$^2$ was determined to provide a relatively unbiased estimate of the model's predictability in the whole population. The model also was cross-validated using the jackknife technique, in which separate predictive equations were derived for a series of data sets, each missing a single subject. The correlation between the predictions for each subject and measured $CL_{CR}$ is an unbiased estimate of the correlation that would be obtained in an independent sample.

The following examples help to exemplify the present invention, but are not intended to limit it in any way.

EXAMPLE 1

Figure 1:
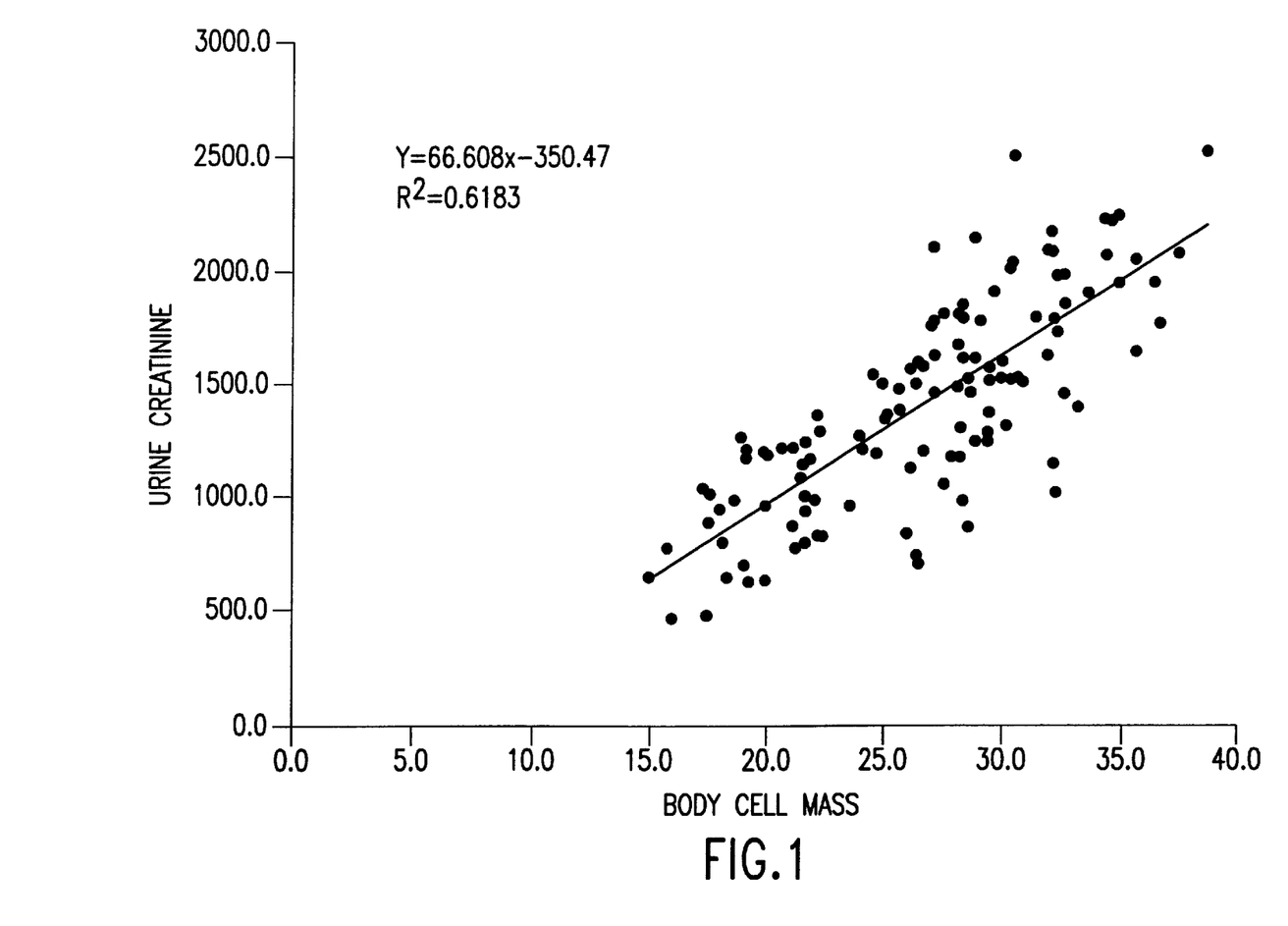
FIG. 1 is a chart illustrating the results of a comparison of creatinine excretion in 24-hour urine collection and BCM estimated by BIA.

Effect of Nutritional Status upon Creatinine Excretion and Creatinine Clearance Total 24-hour urinary creatinine excretion, a reflection of skeletal muscle mass, was compared to weight, IBW, percent IBW, BMI and BCM estimated by BIA (Table 1). The results show that BCM had the strongest correlation with total urinary creatinine ($r^2=0.62$, $p<0.001$) and all other variables, with the exception of percent IBW, had weaker but significant relationships to total creatinine output. FIG. 1 illustrates the graph of the relationship between BCM and urinary creatinine excretion. These results demonstrate the close relationship between skeletal muscle mass, as reflected by total urinary creatinine and BCM, as determined by BIA.

Creatinine clearance was compared to nutritional status, as represented by weight, IBW, percent IBW, BMI (wt/ht$^2$) and BCM. Among these variables, BCM also bore the closest relationship to $CL_{CR}$ ($r^2=0.25$, $p<0.001$) (Table 1). The relationship between $CL_{CR}$ and BMI showed a trend towards significance ($p=0.10$), while no significant relationship between body weight as percent of ideal and $CL_{CR}$ was found. The slope of the relationship was positive for all of the variables examined, indicating that renal function varies significantly with nutritional status, specifically BCM, and is diminished in malnourished people.

TABLE 1

RELATIONSHIPS BETWEEN URINARY CREATININE EXCRETION, CREATININE CLEARANCE AND NUTRITIONAL STATUS: LINEAR REGRESSION

| | Equation | $r^2$ | SEE | p |
|---|---|---|---|---|
| Urinary Creatinine Excretion | | | | |
| Weight | 17.0(Wt) + 202 | 0.28 | 390 | <0.001 |
| Ideal body weight | 25.0(IBW) − 301 | 0.30 | 395 | <0.001 |
| Percent ideal body weight | 1.7(PIBW) + 1255 | 0.001 | 461 | =0.35 |
| Body mass index | 25.6(BMI) + 835 | 0.056 | 448 | =0.005 |
| Body cell mass | 66.6(BCM) − 350 | 0.615 | 286 | <0.001 |
| Creatinine Clearance | | | | |
| Weight | 0.90(Wt) + 51.4 | 0.12 | 30.3 | <0.001 |
| Ideal body weight | 1.3(IBW) + 18.2 | 0.16 | 29.5 | <0.001 |
| Percent ideal body weight | 0.06(PIBW) + 102 | 0.007 | 32.4 | =0.64 |
| Body mass index | 1.07(BMI) + 83.5 | 0.014 | 32.0 | =0.10 |
| Body cell mass | 3.0(BCM) + 27.8 | 0.25 | 27.9 | <0.001 |

Urinary creatinine excretion in mg, creatinine clearance in ml/min
$r^2$ = correlation coefficient
SEE = standard error estimate
p = statistical significance

EXAMPLE 2

Estimation of Creatinine Clearance by the Cockcroft-Gault Equation

Figure 2A:
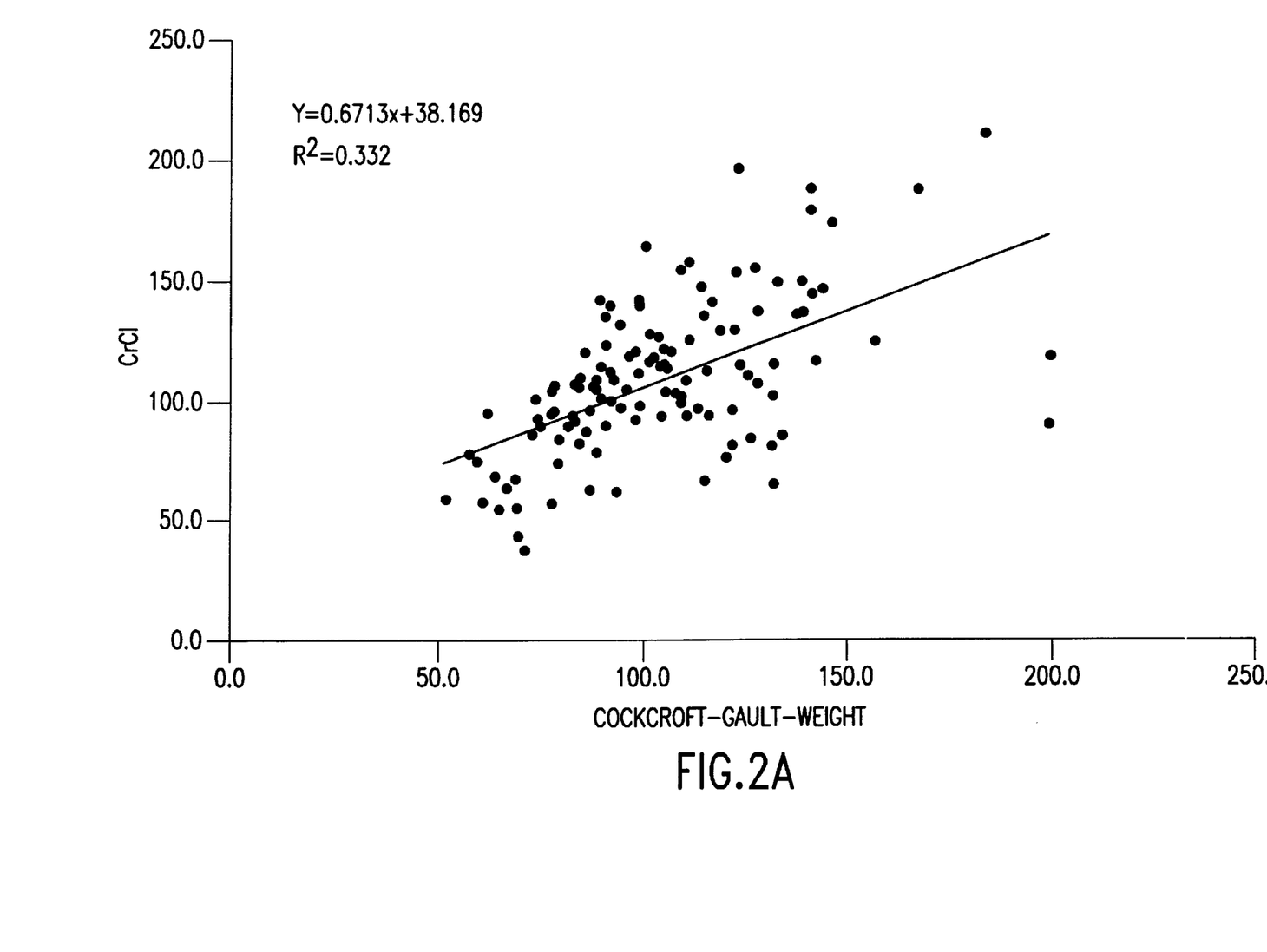
FIG. 2a is a chart illustrating the results of a comparison of $CL_{CR}$ by 24-hour urine collection and prediction of the value by the Cockcroft-Gault (C-G) equation using actual body weight.
Figure 2B:
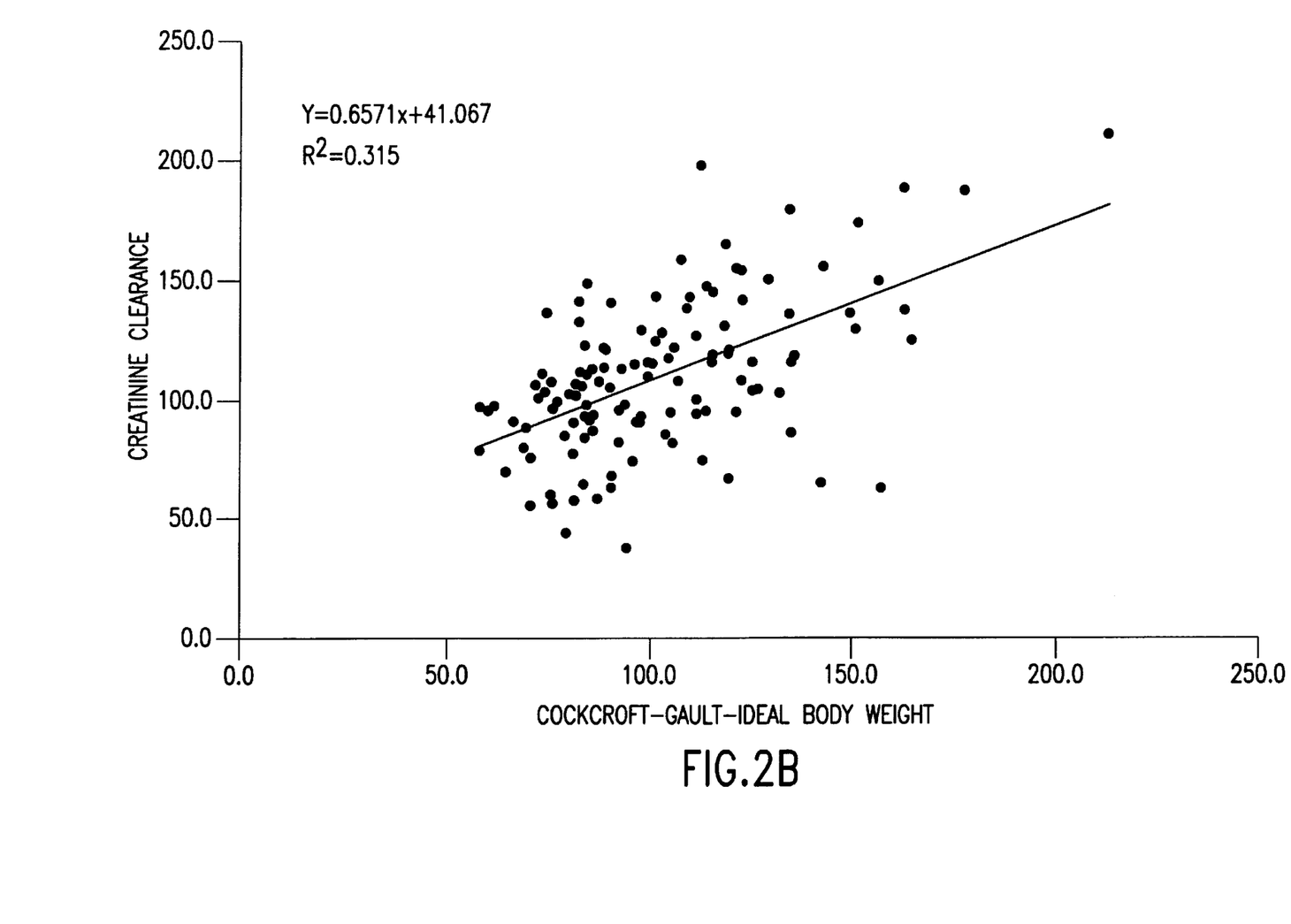
FIG. 2b is a chart illustrating the results of a comparison of $CL_{CR}$ by 24-hour urine collection and prediction of the value by the C-G equation using IBW.

In the study, measured $CL_{CR}$ correlated with $CL_{CR}$ derived from the C-G equations using either actual weight ($R^2=0.32$, $p<0.001$) or with IBW ($R^2=0.29$, $p<0.001$), as shown in FIGS. 2a and 2b, respectively. $R^2$ refers to a multiple correlation between one dependent variable and several independent variables. The relationships among measured $CL_{CR}$ and the individual components of the C-G equation, including either actual weight or IBW, age, $S_{CR}$, and height, the latter used in the determination of IBW, were analyzed by stepwise multiple regression (Table 2). In the C-G equation using actual body weight, all components made independent, significant contributions to the model. Age did not have a significant, independent effect on the prediction model in the C-G prediction using IBW. Height did not contribute to the model independently of IBW.

Figure 3A:
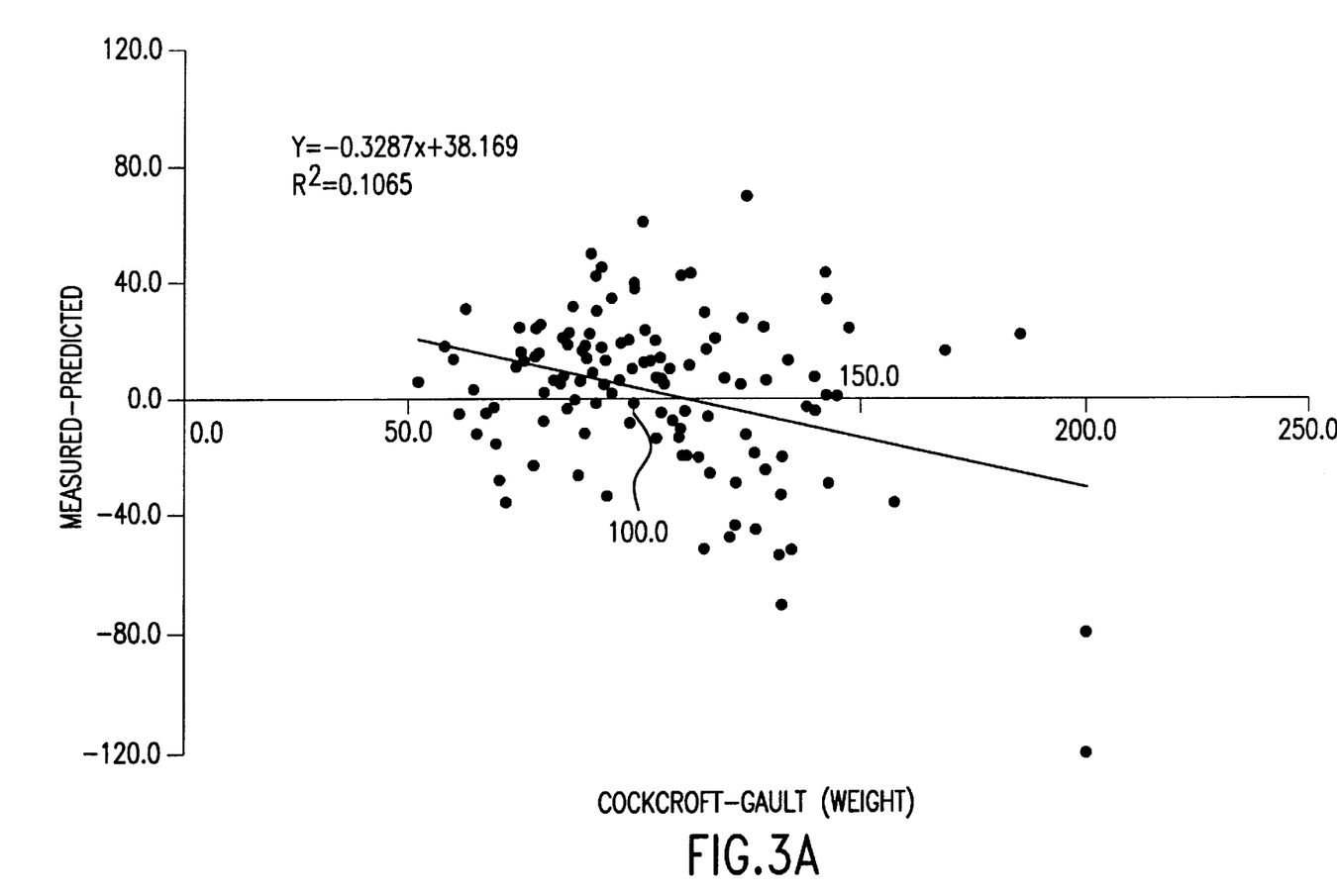
FIG. 3a is a chart illustrating the results of a comparison of the difference between measured and estimated $CL_{CR}$ and prediction of the value by the C-G equation using actual body weight.
Figure 3B:
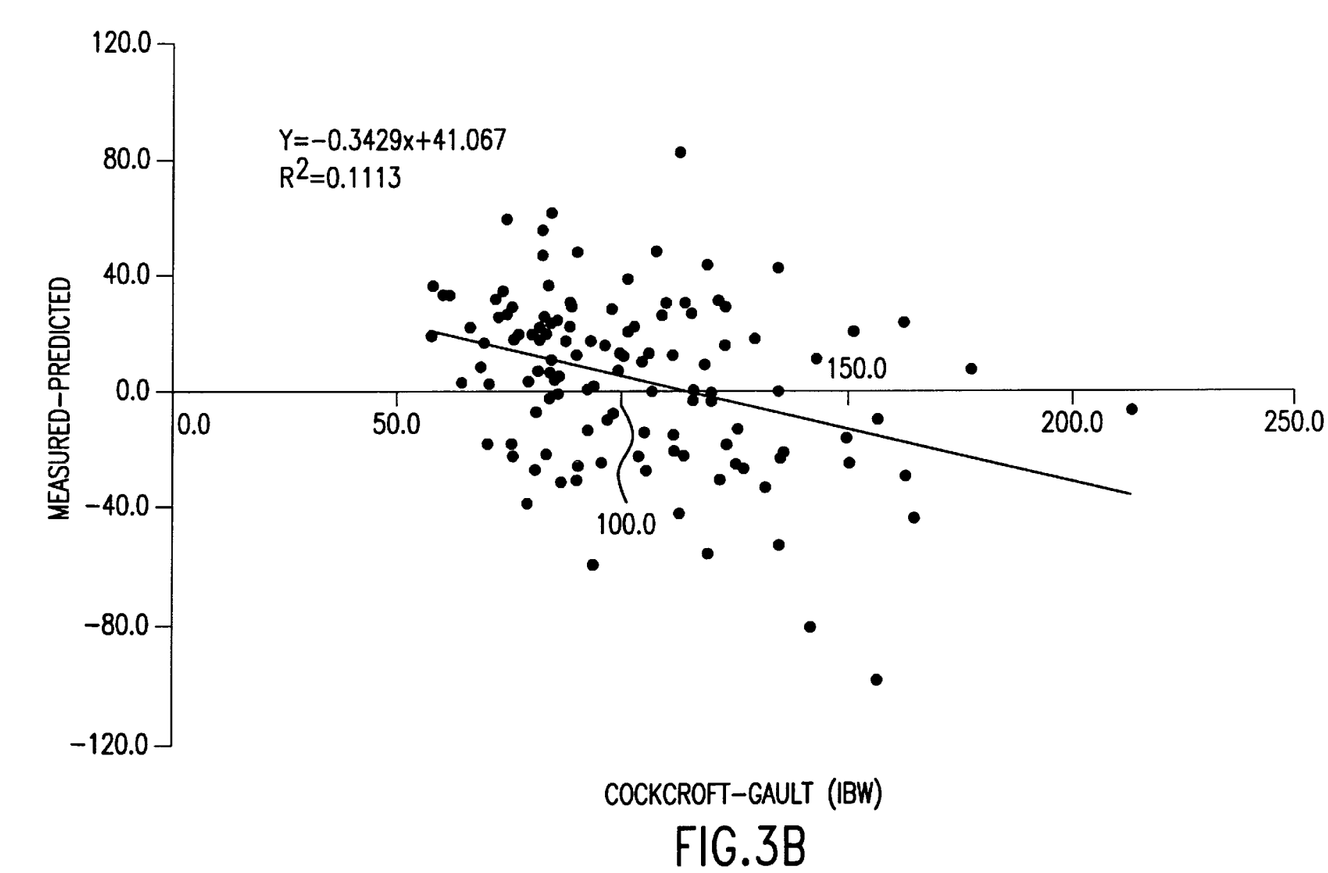
FIG. 3b is a chart illustrating the results of a comparison of the difference between measured and estimated $CL_{CR}$ and prediction of the value by the C-G equation using IBW.

Residual analyses were performed to determine if predictive accuracy varied over the range of results of either measured or predicted $CL_{CR}$. The results indicated that either form of the C-G equation, using either weight or IBW, gave systematic errors in prediction. FIGS. 3a and 3b plot the difference between measured and predicted $CL_{CR}$ versus the predicted values. FIG. 3a illustrates the predictive equation using actual body weight while FIG. 3b illustrates the equation using IBW. Both plots of residual versus predicted value had negative slopes, indicating that the equation overestimated measured $CL_{CR}$ at low values and underestimated $CL_{CR}$ at high values. The error in prediction, as a percentage of the measured value, also increased as $CL_{CR}$ decreased.

Figure 4A:
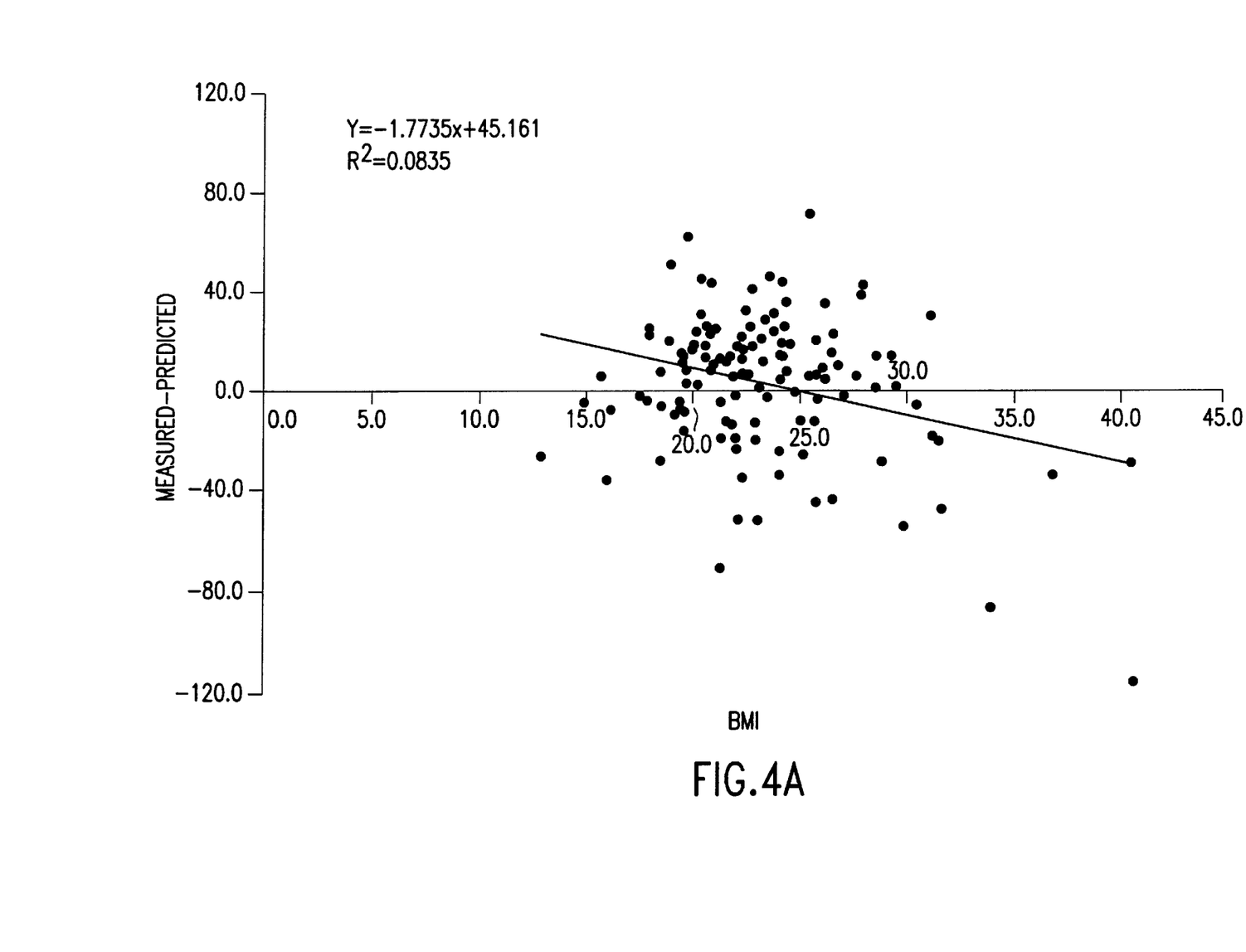
FIG. 4a is a chart illustrating the results of a comparison of the difference between measured and estimated $CL_{CR}$ using the C-G equation with actual body weight and body mass index (BMI)
Figure 4B:
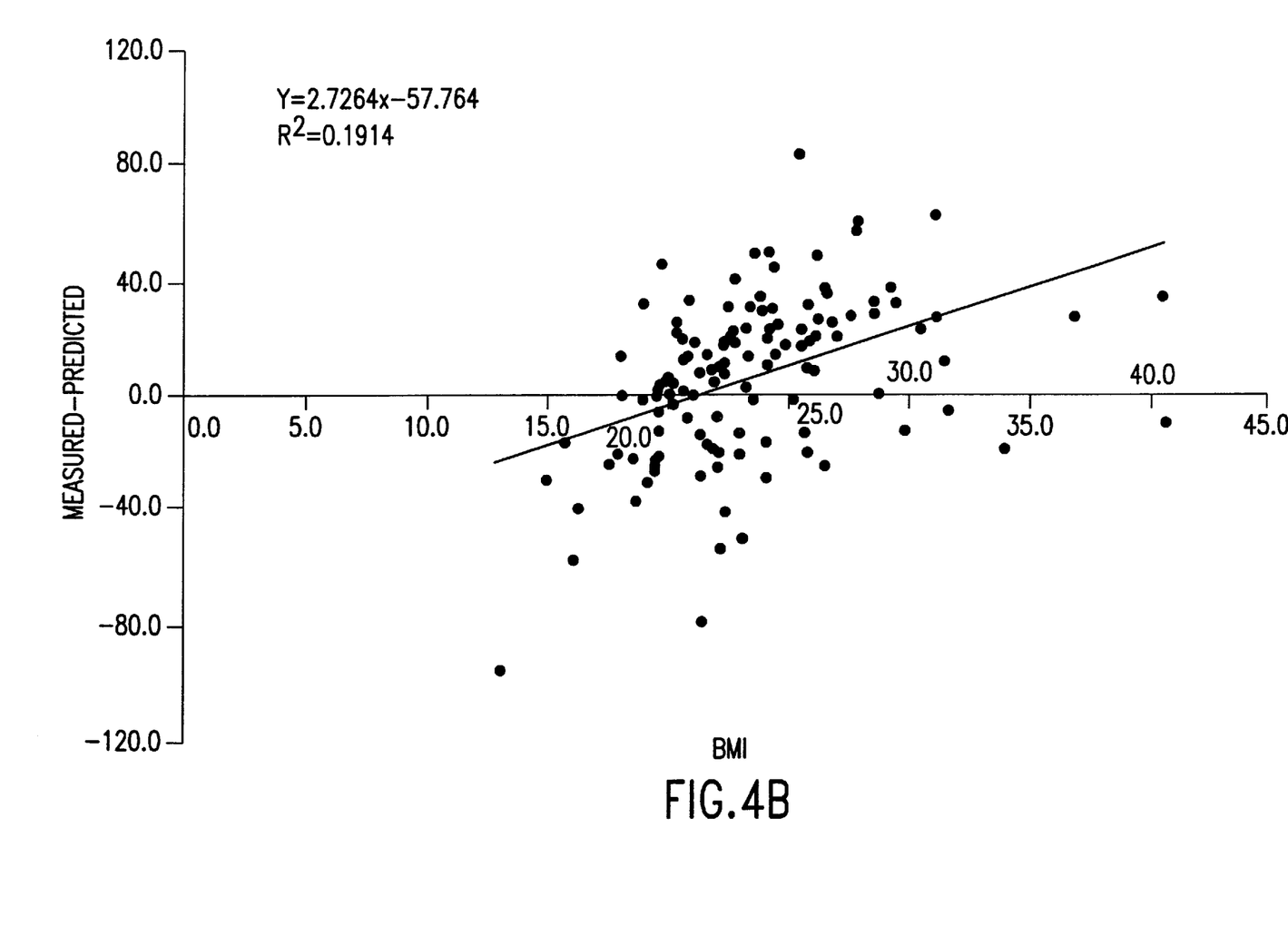
FIG. 4b is a chart illustrating the results of a comparison of the difference between measured and estimated $CL_{CR}$ using the C-G equation with IBW and BMI.

A systematic error also was found in the Cockcroft-Gault prediction, when analyzed as a function of nutritional status, defined as percent IBW, BMI or BCM. For example, in the analysis of measured minus predicted $CL_{CR}$ versus BMI plotted in FIGS. 4a and 4b, the errors in the two equations occurred in opposite directions. The C-G equation using actual body weight, underestimated $CL_{CR}$ in subjects with low BMI values and overestimated the value in subjects with high BMI values, as shown in FIG. 4a. In contrast, the C-G equation using IBW overestimated $CL_{CR}$ in subjects with low BMI values and overestimated the value in subjects with high BMI values, as illustrated in FIG. 4b. Plotting measured minus predicted $CL_{CR}$ versus percent IBW or BCM provide the same results.

TABLE 2

Relationships Between Measured Creatinine Clearance and Other Measurements

| Variable | Regression Coefficient | Partial r | p |
|---|---|---|---|
| Cockcroft-Gault Equation Using Body Weight | | | |
| Weight | 0.94 | 0.15 | <0.001 |
| Serum creatinine | −77.5 | 0.11 | <0.001 |
| Sex | −35.9 | 0.14 | <0.001 |
| Age | −0.61 | 0.03 | =0.03 |
| Height | 6.50 | 0.01 | =0.16 |
| Cockcroft-Gault Equation using Ideal Body weight | | | |
| Ideal body weight | 1.14 | 0.17 | <0.002 |
| Serum creatinine | −64.4 | 0.12 | <0.001 |
| Sex | −19.3 | 0.03 | =0.03 |
| Age | −0.36 | 0.01 | =0.21 |
| Height | −54.1 | 0.01 | =0.31 |
| Predictive Model using Body Cell Mass | | | |
| Body cell mass | 4.74 | 0.26 | <0.001 |
| Serum creatinine | −98.1 | 0.26 | <0.001 |
| Sex | −3.59 | 0.001 | =0.62 |
| Age | −0.34 | 0.008 | =0.15 |
| Height | −0.10 | 0.0004 | =0.74 |

Stepwise multiple regression with measured creatinine clearance as the dependent variable. Body weight, ideal body weight and body cell mass in kg, age in years, height in cm. For sex, males=1, females=2.

EXAMPLE 3

Estimation of Creatinine Clearance Using Body Cell Mass

Figure 5A:
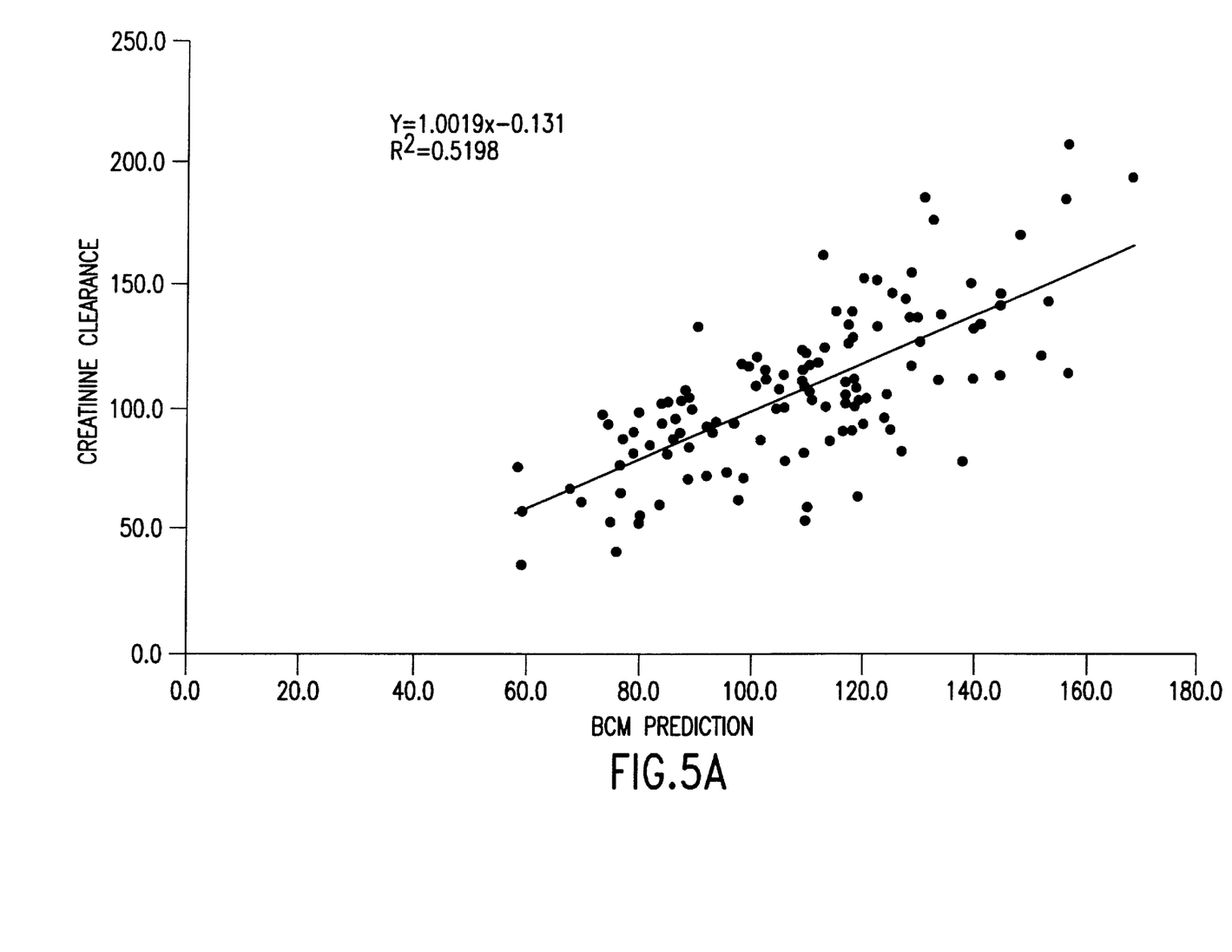
FIG. 5a is a chart illustrating the results of a comparison of $CL_{CR}$ measured by 24-hour urine collection and $CL_{CR}$ predicted using BCM, estimated by BIA, and serum creatinine concentration ($S_{CR}$)
Figure 5B:
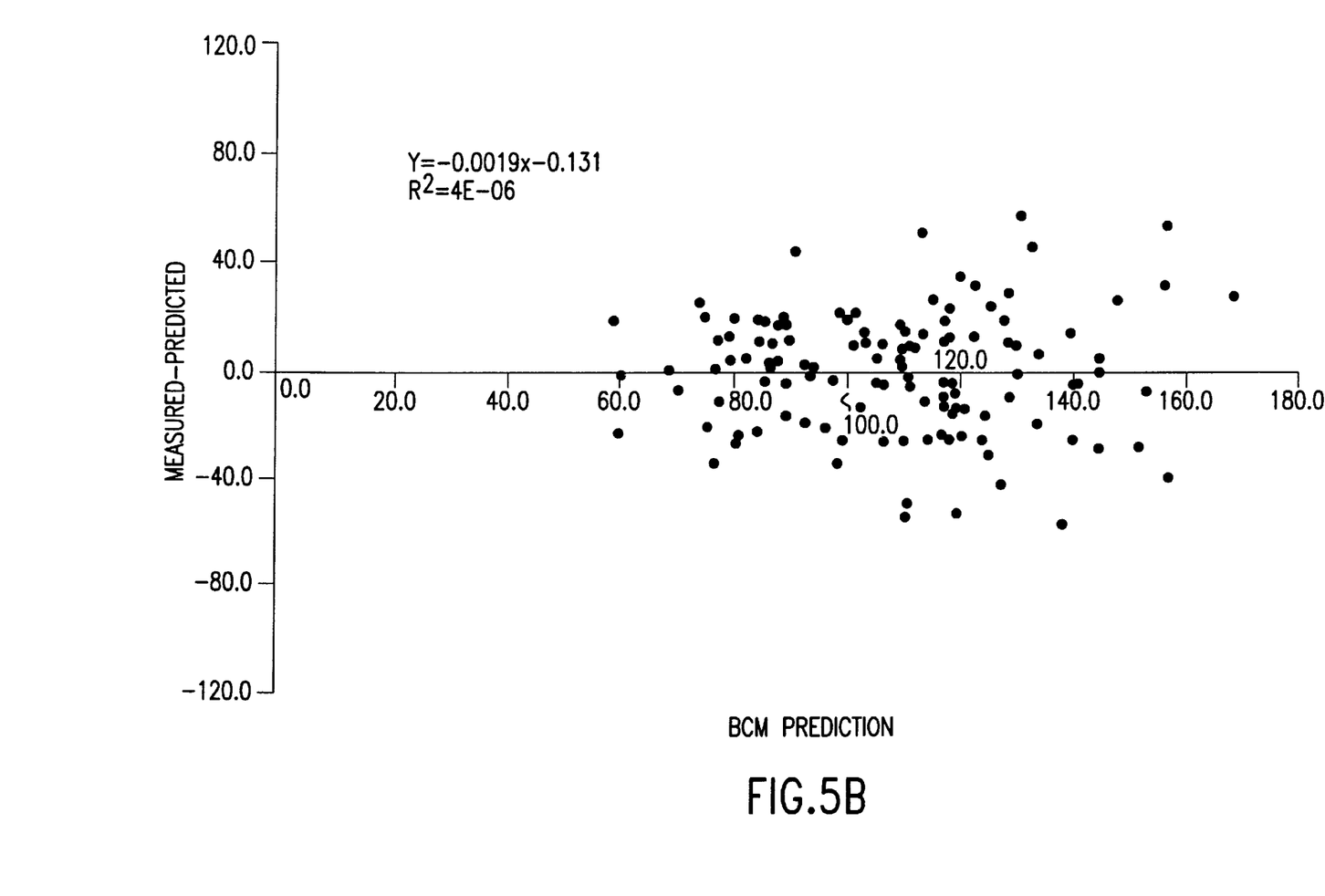
FIG. 5b is a chart illustrating the results of a comparison of the difference between measured and estimated $CL_{CR}$ and prediction of $CL_{CR}$ using BCM, estimated by BIA, and $S_{CR}$.
Figure 5C:
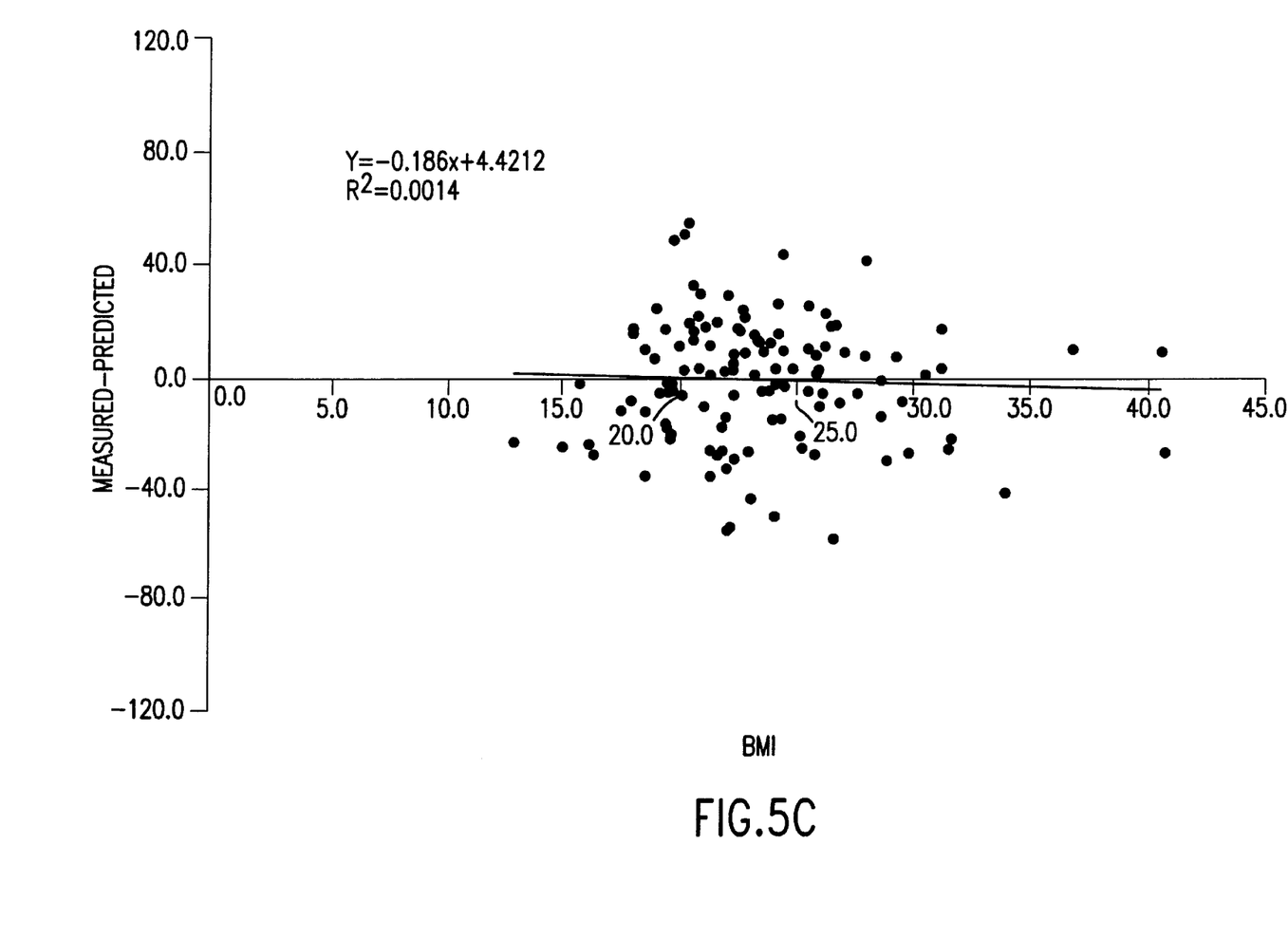
FIG. 5c is a chart illustrating the results of a comparison of the difference between measured and estimated $CL_{CR}$ (using BCM and $S_{CR}$) and BMI.

Given the errors in predicted $CL_{CR}$ using either form of the C-G equation, predictive equations were derived for $CL_{CR}$ using BCM, calculated from BIA. As shown in Table 2, BCM correlated significantly with $CL_{CR}$ ($r^2=0.25$, $p<0.001$). In FIG. 5a, measured $CL_{CR}$ is plotted against predicted $CL_{CR}$ using the following equation: $CL_{CR} = 4.81$ (BCM)$-97.11(S_{CR})+69.7$ ($R^2=0.51$, $p<0.001$) in accordance with the present invention. The addition of $S_{CR}$ substantially improved the accuracy of the $CL_{CR}$ prediction. Addition of height, age, sex, and disease group (control vs. HIV+) had no significant, independent effects upon the prediction of $CL_{CR}$. The adjusted $R^2$, representing an unbiased estimate of the model in the whole population, was similar to the raw $R^2$, reflecting the relative large study group and few variables used in the model. Residual analyses showed no evidence of systematic error, when measured minus predicted results were plotted against predicted $CL_{CR}$, as shown in FIG. 5b, and against BMI, as shown in FIG. 5c. Similarly, no systematic errors are seen when the residual value is plotted as a function of IBW or BCM. Thus, a predictive model for $CL_{CR}$ based upon BCM and $S_{CR}$ shows a closer relationship to actual $CL_{CR}$ than do estimates made using the C-G equation. Furthermore, this predictive model does not have a systematic error in prediction across the range of possible body composition values.

The predictive equation of the present invention was evaluated using the jackknife technique, as described in the methods. The correlation between measured $CL_{CR}$ and the predicted values was very similar to that found in the initial model ($R^2=0.52$). This result suggests that similar correlations would be found if predictions and actual measurements of $CL_{CR}$ are made on an independent study group.

Discussion of the Examples

Assessment of $CL_{CR}$ is important in many areas of clinical medicine, most notably in determining the proper doses of certain medications. If a drug or its active metabolites undergo renal clearance, diminished renal function may lead to elevated serum concentrations and increased risk of toxicity, unless the dose is adjusted for renal function. Conversely, inadequate doses may be subtherapeutic in patients whose renal function is better than estimated.

Many patients require urgent administration of potentially toxic medications, such as aminoglycosides, antifungal or antiviral agents in a time frame that does not allow prior measurement of $CL_{CR}$. For this reason, a number of predictive equations have been developed to predict $CL_{CR}$. However, as indicated above, many of the published equations, including the C-G equation, demonstrate considerably predictive errors.

The measurement of actual body weight or calculation of IBW does not distinguish between BCM, fat and extracellular water. The relationships among these body compartments are altered by disease and in obesity. BCM is considered of key importance in clinical nutrition since it is the compartment responsible for all metabolic activity. Severe malnutrition invariably is associated with BCM depletion. The kidney is a component of the BCM. For these reasons, the relationship between BCM and renal function was examined in this study.

The present invention provides that: (1) renal mass is a constant proportion of BCM in the absence of intrinsic renal disease, (2) renal mass is directly related to $CL_{CR}$ and (3) proportionate changes in BCM and $CL_{CR}$ occur as a result of malnutrition. BCM has been shown, in Example 1, to be more closely related to $CL_{CR}$, as well as total urinary creatinine excretion, than was weight or IBW. Variation in body fat content or hydration status may explain much of the difference.

The present invention provides that the standard (C-G) equations currently in use have a systematic error in the prediction of $CL_{CR}$ that differ, based upon the use of ideal or actual body weight in the equation. As shown in Example 2, both equations overestimate $CL_{CR}$ at low values of measured $CL_{CR}$ and underestimate $CL_{CR}$ at high values as shown in FIGS. 3a and 3b. However, the equation using IBW overestimates $CL_{CR}$ in malnourished people, expressed as subnormal BMI, percent IBW or BCM, and underestimates the measured value in overnourished (obese) people as shown in FIGS. 4a and 4b. In contrast, the equation using actual body weight has the opposite effect. Thus, the predictive accuracy of these equations falls as nutritional status deviates from normal with possible increased risks of toxicity in malnourished patients and subtherapeutic dosing in obese patients.

The equation of the present invention (shown as derived in Example 3), which uses BCM to predict $CL_{CR}$ gave estimates with higher correlation coefficients than the C-G equation, consistent with its derivation from the data in these subjects. Importantly, the prediction model using BCM did not have a systematic error when analyzed in reference to predicted or measured $CL_{CR}$ or to nutritional status, expressed as percent IBW, BMI or BCM. While age and sex influence renal function, justifying their inclusion in many predictive equations, they had no independent predictive value in the present invention which relies on BCM. It is likely that age and sex affect renal function solely through their influences on BCM. Adjusting low $S_{CR}$ to 1.0 mg/dL does not improve the prediction. The standard error of the prediction is about 22 ml/min or about 21% of the average value, which must be viewed in the context that the reproducibility of 24-hour $CL_{CR}$ is about 20%. Thus, an increasingly available bedside technology can be used to improve estimation of $CL_{CR}$ in seriously ill patients.

There are several potential causes for discrepancies in predicted and measured $CL_{CR}$, some of which are related to variance in the criterion measurement. Differences of 10–20% on repeat testing are reported in the standard 24-hour urine collection method of determining $CL_{CR}$ or $CL_{IN}$. Furthermore, errors in the measurement of $S_{CR}$ also may have a major effect on the calculation. The smallest reportable difference in reported results, 0.1 mg/dL, would cause a 7–20% change in $CL_{CR}$ within the range of $S_{CR}$ values in this study group (0.5–1.5 mg/dL). In addition, the completeness of urine collection may also affect studies. In addition, estimation of renal function by $CL_{CR}$ is based upon the assumptions that the subject is in steady state, that skeletal muscle mass is a constant percentage of weight, and that fractional skeletal muscle turnover is constant. These assumptions may not be true, particularly in acutely or chronically ill patients whose skeletal muscle mass may be disproportionately low, or catabolic patients in whom fractional muscle breakdown and creatinine production may be elevated. Additionally, the relationship between weight and skeletal muscle mass will vary with hydration status and is altered in obesity, states of fluid overload or dehydration. Dehydration also may independently affect $CL_{CR}$ through effects on renal perfusion.

As stated in the background section, the largest clinical experience of nephrotoxicity associated with medication is aminoglycoside toxicity. Its reported incidence ranges from 0 to 50%, with rates in most studies in the 5 to 25% range. The wide range of results likely reflects the different populations studied. During a recent one month period, the records of 33 patients at St. Luke's-Roosevelt Hospital Center (SLRHC) who received aminoglycosides were reviewed. In 4 of 33 patients (12%), the $S_{CR}$ increased by over 50%, within a period from within 3 days of initiation of aminoglycoside therapy, up to a week after therapy was discontinued. These results indicate that our institutional experience falls in the range observed in the above studies. No studies have specifically examined the relationship between nutritional status and the risk of aminoglycoside toxicity. There may be similar increased vulnerabilities of malnourished subjects to other agents.

A recent paper demonstrated that once-daily dosing of aminoglycosides is as safe as administration of multiple doses, and is more cost-effective. However, errors in estimating renal function could have the same influence on renal toxicity, irrespective of the number of doses given per day. Improving the prediction of $CL_{CR}$ could decrease the incidence of nephrotoxicity, independent of dosing frequency, and lead to improved outcomes, including cost savings.

While the foregoing indicates the preferred embodiments of the invention claimed below, those skilled in the art will appreciate that there are variations of the inventor's disclosure which do not depart from the scope of the invention herein. For example, isotope dilution analysis, or the like, may be substituted for bioimpedance analysis. BIA may be based on modelling the human body using segmental analysis or the like. Additionally, different amperages and frequencies may be used during BIA, all of which are within the skill of those in the art to readily determine.

Other methods may be used to estimate BCM, including, but not limited to, analysis of total body potassium, intracellular water volume, and total body nitrogen. Also, given the teachings of the present invention, different mathematical equations other than those specifically referred to above may be readily derived by those skilled in the art to determine BCM from BIA.

We claim:

1. A method for estimating creatinine clearance in a subject, said method comprising the steps of:
   calculating a value for body cell mass of said subject;
   estimating creatinine clearance of said subject as a function of said value; and
   measuring the serum creatinine concentration of said subject.

2. The method of claim 1 wherein said calculating step includes the step of measuring said value using bioimpedance analysis.

3. The method of claim 1 wherein said estimating step comprises determining creatinine clearance according to the equation:

$$CL_{CR}=4.81\times(BCM)-97.11\ (S_{CR})+69.7$$

where:
   $CL_{CR}$=creatinine clearance;
   BCM=body cell mass (kg); and
   $S_{CR}$=serum creatinine concentration (mg/dl).

4. A method for predicting creatinine clearance in a subject, said method comprising the steps of:
   calculating the value of body cell mass of the subject using bioimpedance analysis;
   measuring the serum creatinine concentration of said subject; and
   determining creatinine clearance according to the equation:

$$CL_{CR}=4.81\times(BCM)-97.11\ (S_{CR})+69.7$$

where:
   $CL_{CR}$=creatinine clearance;
   BCM=body cell mass (kg); and
   $S_{CR}$=serum creatinine concentration (mg/dl).

5. The method of claim 4 wherein the calculating step includes the step of determining body cell mass according to the following equations:

$$BCM=0.76[(59.06)Ht^{1.60}/Xc_p^{0.50}]+18.52(Wt)-386.66\ \text{(for males)};$$
or
$$BCM=0.96[(1.30)Ht^{2.07}/Xc_p^{0.36}]+5.79(Wt)-230.51\ \text{(for females)};$$

where:
   Ht=height (cm);
   $Xc_p$=parallel transformed reactance (ohms); and
   Wt=weight (kg).

6. A method for accurately prescribing medication comprising the steps of:
   determining a value for the body cell mass of a subject;
   determining a value for the serum creatinine concentration of the subject;
   estimating creatinine clearance of said subject from said values of body cell mass and serum creatinine concentration; and
   prescribing an appropriate dosage of medication in accordance with said estimated creatinine clearance.

7. The method of claim 6 wherein the step of determining said body cell mass comprises the step of using bioimpedance analysis.

8. The method of claim of claim 6 wherein said measuring of body cell mass comprises the following formulas to determine values for body cell mass:

$$BCM=0.76[(59.06)Ht^{1.60}/Xc_p^{0.50}]+18.52(Wt)-386.66\ \text{(for males)};$$
or
$$BCM=0.96[(1.30)Ht^{2.07}/Xc_p^{0.36}]+5.79(Wt)-230.51\ \text{(for females)};$$

where:
   Ht=height (cm);
   $Xc_p$=parallel transformed reactance (ohms); and
   Wt=weight (kg).

9. The method of claim 6 wherein the step of estimating the creatinine clearance of said subject comprises using the following formula:

$$CL_{CR}=4.81\times(BCM)-97.11\ (S_{CR})+69.7$$

where:
   $CL_{CR}$=creatinine clearance;
   BCM=body cell mass (kg); and
   $S_{CR}$=serum creatinine concentration (mg/dl).

* * * * *